United States Patent
Huff et al.

(10) Patent No.: US 8,515,696 B2
(45) Date of Patent: Aug. 20, 2013

(54) METHOD AND SYSTEM FOR ACQUIRING AND ANALYZING COIL DATA

(75) Inventors: Steven James Huff, Watertown, WI (US); Kamal Mannar, Atlanta, GA (US)

(73) Assignee: General Electric Company, Schenectady, NY (US)

( * ) Notice: Subject to any disclaimer, the term of this patent is extended or adjusted under 35 U.S.C. 154(b) by 402 days.

(21) Appl. No.: 13/009,942

(22) Filed: Jan. 20, 2011

(65) Prior Publication Data
US 2012/0191383 A1    Jul. 26, 2012

(51) Int. Cl.
*G01R 31/00*    (2006.01)

(52) U.S. Cl.
USPC .......................................................... 702/58

(58) Field of Classification Search
USPC .................................................................. 702/58
See application file for complete search history.

(56) References Cited

U.S. PATENT DOCUMENTS
2009/0278536 A1* 11/2009 Winkelmann et al. ........ 324/309

OTHER PUBLICATIONS

"Protection and Performance Philips Remote Services." 2008 Koninklijke Philips Electronics N.V.
Siemens White Paper Pamphlet; Dec. 2009; www.siemens.com/healthcare.

* cited by examiner

*Primary Examiner* — Stephen Cherry
(74) *Attorney, Agent, or Firm* — Global Patent Operation (57) ABSTRACT

A system for acquiring and analyzing fault conditions for at least one coil of Magnetic Resonance Imaging (MRI) system. Each of the at least one coils is electrically connected through a transmit/receive (T/R) bias circuit to an interface. The system has a central processing unit with a processor configured to execute programmable instructions which when executed by the processor cause the processor to conduct circuit tests at predetermined intervals for the at least one coil, acquire data for the at least one coil to construct a data log with a plurality of input events, and algorithmically filter and analyze the plurality of input events to create an output configured to predict a failure event of the at least one coil. A method for analyzing and acquiring fault conditions is also provided.

20 Claims, 4 Drawing Sheets

METHOD AND SYSTEM FOR ACQUIRING AND ANALYZING COIL DATA

BACKGROUND OF THE INVENTION

1. Field of the Invention

The field of the invention relates to Magnetic Resonance Imaging ("MRI") generally, and more particularly to certain new and useful advances in analyzing multi-coil transmit/receive ("T/R") bias parametric data, of which the following is a specification, reference being had to the drawings accompanying and forming a part of the same.

2. Description of Related Art

Magnetic resonance (MR) imaging is a technique in which an object is placed in an electromagnetic field and subjected to pulses of the electromagnetic field at a particular frequency. The pulses cause nuclear magnetic resonance in the object and the spectra obtained thereby is processed numerically to form cross-sectional images of the object. MR imaging is especially useful for medical or veterinary applications because different living tissues emit different characteristics of resonance signals, thus enabling visualization of the different living tissues in the obtained image. An MRI apparatus thus operates in general by the application of a radio frequency (RF) electromagnetic field in the presence of other magnetic fields, and the subsequent sensing and analysis of the resulting nuclear magnetic resonances induced in the body.

Phased array multi-coils can be used in MRI to improve the signal-to-noise ratio (SNR) of images. The multi-coils allow large field of view imaging with the SNR of a small surface coil. Separate images are acquired and reconstructed from each of the elements in the multi-coil array. These separate images are then combined into a single image, with each coil dominating the spatial regions where its SNR is the highest. Typically, systems which employ a multi-coil array have an interface connected to a scanner. Each coil of the multi-coil array is electrically connected through a transmit/receive ("T/R") bias circuit to an RF switch in the interface. The RF switch typically has a plurality of outputs that are connected to a plurality of receiver preamplifiers in the scanner. It is known in the industry that multi-coils have high parts usage, are high in replacement cost and cause an inordinately high workflow disruption.

System failures can cause a myriad of problems for their users including but limited to decreased image quality and complete inhibition of scanning. Generally, reasons for multi-coil system failures fall into one of three categories: (1) Physical damage to a coil, cable or connector, (2) T/R bias circuit failures, or (3) signal loss, noise or shadowing in images. When the failure is operator induced, it is typically due to the operator not making a suitable physical connection between the coil connectors and the system connector.

T/R bias circuit failures may be due to hardware failures or pending hardware failures in the T/R circuitry itself. If the failure is due to hardware malfunctions, it is often times difficult to tell if it is a true hardware failure or merely an operator induced failure. Also, often times there may be signs that the T/R circuitry is failing, and if not dealt with appropriately, may lead to system degradation or system failure and, in turn, ultimately lead to workflow disruption.

Presently, certain systems may be equipped with data monitoring systems that track and store fault data associated with the system. For example, Phillips Healthcare, in pamphlet number 4522 962 36291/800 ©August 2008, provides a remote services system that shares data and monitors equipment from a remote location. In the system provided by Philips, adjustments to equipment may be made remotely of scheduled to be completed during routine service calls. Siemens AG, in White Paper Pamphlet published in December 2009, discloses a remote systems analysis capable of detecting and repairing problems with equipment, in some instances. For example, in this pamphlet at page 6, Siemens describes a system for a CT scanner in which the scanner is preloaded with more than 10 sensors that are constantly monitoring the tube functions, the sensors then communicate any detected problems back to a service team.

There are many drawbacks with the above-described ad hoc approaches. One problem it is such approaches focus on the technician's ability to recognize, from a potentially complicated data set, a potential fault condition. Another problem is that even if the technician properly recognizes a fault condition, it assumes he or she will take the proper remedial steps, and that it would be extremely costly and labor intensive for a technician to constantly monitor and analyze data from the T/R circuitry, so much so that it is not feasible. In the case of systems that electronically monitor data, the analysis is not forward thinking and predicative, but rather reactive to a problem that may be taking place at that given time.

Accordingly, to date, no suitable system or method for monitoring, acquiring and analyzing multi-coil fault data exists.

BRIEF SUMMARY OF THE INVENTION

The present disclosure describes embodiments for analyzing multi-coil T/R bias parametric data. Embodiments of the invention provide a system and method to proactively predict a failure event of an MR coil before the MR coil fails so that a technician may respond appropriately, thus eliminating work-flow disruptions. Embodiments of the invention also algorithmically categorize types of faults, and in particular, filter a hardware fault from an operator induced fault.

In one embodiment, a method comprises conducting circuit tests on at least one MR coil (which are typically part of a coil array) at predetermined intervals or upon the happening of predetermined events, and constructing data logs for each coil. Each data log is processed, filtered and analyzed in near real-time, and in one embodiment, the processor is configured to detect unique parametric data signatures that identify the possibility of a pending failure of the coil TR bias or related circuitry, also referred to as an output event. Where appropriate, the system notifies a technician of the output event and that a coil requires service. Because the technician can respond prior to the coil malfunction in its entirety, the user is saved from workflow disruptions and prohibitive costs.

Embodiments of the invention thus differ from and improve over prior designs which rely on reactive servicing of MR coils because they are capable of eliminating workflow disruptions entirely, whereas the prior art systems and methods teach monitoring the MR coil and alerting a technician after the coil has already failed.

Another benefit over and difference from prior approaches is that embodiments of the invention monitor coils for failures and alert technicians as to these failures before a critical failure occurs, thus minimizing or eliminating workflow disruptions.

Accordingly, a system and method is provided for acquiring and analyzing fault conditions for at least one coil of an Magnetic Resonance imaging (MRI) system, each of the at least one coils of the multi-coil array being electrically connected through a transmit/receive (T/R) bias circuit to an interface, the system having a central processing unit having a computer-implemented graphical user interface, and a processor configured to execute the predictive algorithm.

BRIEF DESCRIPTION OF THE DRAWINGS

Other features and advantages of the disclosure will become apparent by reference to the accompanying drawings, in which.

Like reference characters designate identical or corresponding components and units throughout the several views, which are not to scale unless otherwise indicated.

DETAILED DESCRIPTION OF THE INVENTION

Embodiments of the invention detect and analyze fault conditions in multi-coil MRI systems. In particular, acquired data for each coil is used to populate a data log with one or more input events. An input event is defined as an instance at which a coil or scanner is plugged in, an exam is completed, a pre-scan occurs, a T/R bias circuit fault, a coil is changed, or a coil or the scanner is unplugged. Thereafter, selected input events are algorithmically filtered and analyzed to produce an output. The output contains data that provides an estimate of when the coil may fail and/or of an event that may cause the coil to fail. This approach is different from prior approaches in that (a) data logs were not constructed or populated with input events, (b) the input events were not filtered and analyzed using predetermined algorithms to produce an output containing an estimate of when a coil might fail and what event(s) might cause the failure. This is advantageous because coils can be repaired or replaced before they fail thereby lessening, if not eliminating, MRI system down-time and workflow disruptions.

Figure 1:
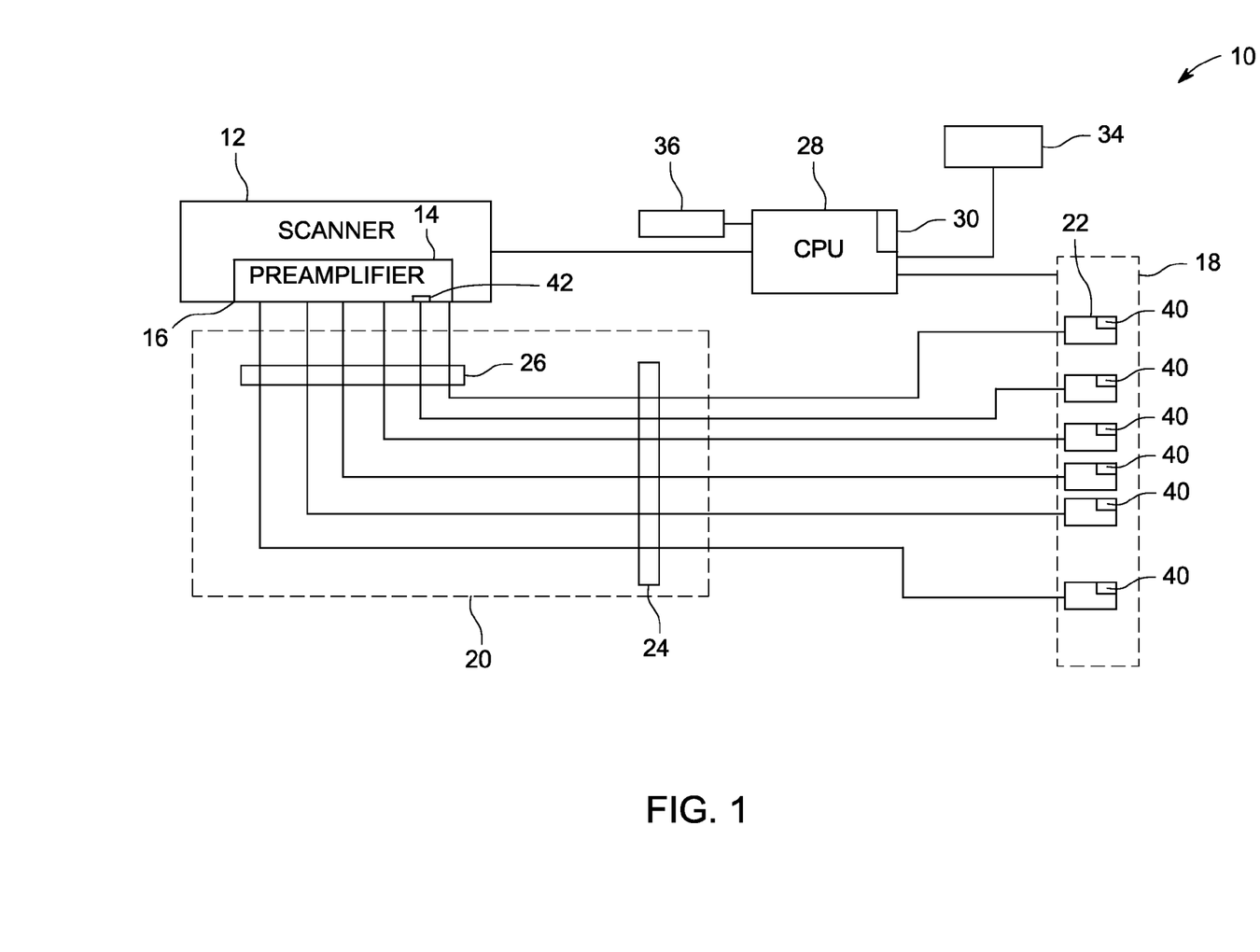
FIG. 1 is a schematic diagram of an exemplary MRI system in accordance with a further embodiment of the present invention.

FIG. 1 shows an exemplary MRI system 10 having a scanner 12, a preamplifier 14 with connection ports 16, and a multi-coil array 18. As used herein, a multi-coil array and/or coil is may be either a transmit/receive coil or a receive only cod that is plugged in to one or more ports 16 of the system 10. The multi-coil array 18 includes plurality of surface coils 22, which can be any number of surface coils N, each coil 22 being connected to the scanner via interface 20. The interface 20 is coupled to a T/R bias circuit 24 and an RF switch 26, and the coils 22 are coupled to the scanner 12 through both the T/R bias circuit 24 and RE switch 26. The MRI system 10 is further connected to a central processing unit (CPU) 28, which is coupled to and in communication with both the coil array 18 and the scanner 12.

CPU 28 may be supplied with multiple processors 32, micro-controllers (e.g., with embedded RAM/ROM) and microprocessors such as programmable devices (e.g., RISC or SISC based, or CPLDs and FPGAs) and devices not capable of being programmed such as gate array ASICs (Application Specific Integrated Circuits) or general purpose microprocessors. The CPU 28 may further be supplied with appropriate hard discs for storage and memory, which may include any suitable computer-readable media, intended for data storage, such as those described above excluding any wired or wireless transmissions unless specifically noted. Processors 32 may also be coupled bi-directionally to CPU 28 to provide additional data storage capacity and may include any of the computer-readable media described above.

The CPU 28 is further connected to a Graphical User Interface (GUI) 34 to enable a user to view the operation of MRI system 10. The CPU 28 is also connected to a network interface 36, which may communicate in either a unidirectional manner or a bi-directional manner, via wireless (via antenna 38) or hard-lined communication with a technician 48 (shown in FIG. 2) in any known manner of communication such as a cellular phone or personal digital assistant (PDA). Embodiments of the present invention, such as those illustratively shown in greater detail in FIGS. 2-5, may be implemented with MRI systems, such as the exemplary MRI system shown in FIG. 1.

Figure 2:
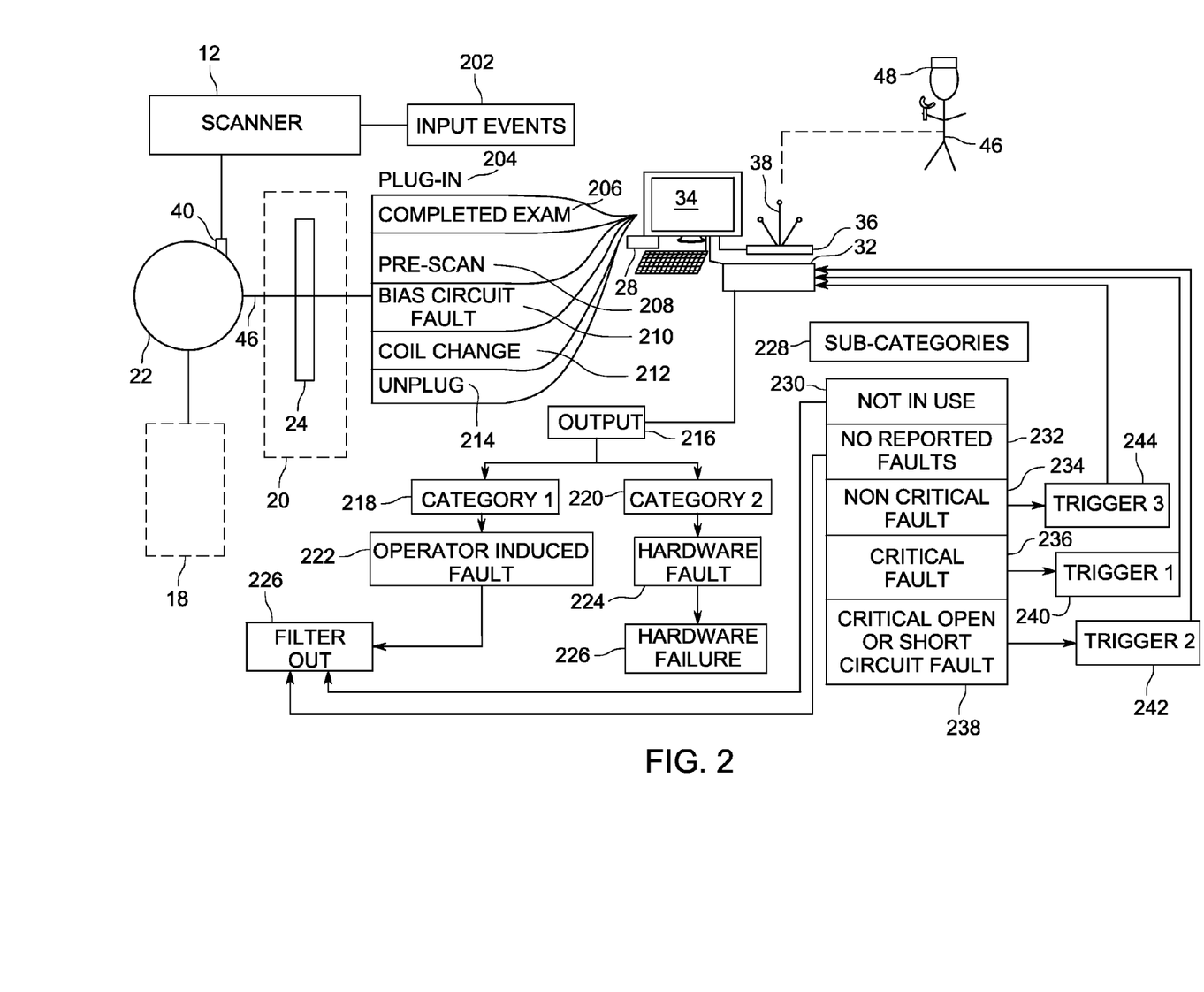
FIG. 2 is a schematic diagram illustrating a system and method for analyzing fault data in accordance with another embodiment of the present invention.

FIG. 2 is a schematic illustration of a system for acquiring and analyzing fault conditions for a coil 22 of an MRI system 10. The CPU 28, through various processors and microcontrollers, conducts circuit tests at predetermined intervals for the multi-coil array 18. A circuit test may include first determining which coils 22 of the array 18 are being used by an operator. As such each coil 18 is provided with a coil identification chip 40 which is coupled to and in communication with the scanner 12 and the CPU 28. Generally, the coil identification chip 40 may be located where the coil 22 connects to the scanner 12 and is also electrically coupled to CPU 28. In this way, each coil 18 has it's own unique serial number, and in the CPU 28, each coil has it's own naming convention. The CPU 28 stores data log file for each particular coil 22, which will be discussed in greater detail with reference to FIG. 3. In some instances, coils may not be provided with a coil identification chip 40 (e.g., coils fabricated before the year 2002). In these instances, coils 22 may either be subsequently fitted with an identification chip 40, or in another embodiment, the CPU 28 may be instructed to ignore those coils that do have an identification chip 40.

Once the CPU 28 determines which of the coils 22 are being used by the operator, the CPU 28 conducts T/R bias open circuit and short circuit tests on each coil. The open and short (i.e. forward and reverse bias) tests are automatically performed as part of a pre-scan process under a set of predetermined conditions, which will be discussed in greater detail, infra. To test the T/R bias the CPU 28 instructs the system to apply forward and reverse bias currents through the coils T/R circuitry and the CPU measures the resulting currents. The currents are then logged to a data file. If the currents are out of a specified predetermined range per coil, an "open" or "short" fault condition is logged in a data log.

To create the data log, the CPU 28 logs data at predetermined inputs events. For example, a data log for each of the coil arrays 18 is developed by automatically logging data at predetermined input events 202. Input events are logged at coil or scanner plug-in 204, a completed exam 206, a pre-scan 208, a T/R bias circuit fault 210, a coil change 212, or an a coil or scanner unplug event 214. For example, when a coil 22 is first plugged in, the CPU 28 logs and stores coil data, which is sent to the CPU from the coil 22 (or in another embodiment, from the scanner 12) through the coil connector cable 46. Steps that are analogous to the ones described above occur when an operator completes an exam 206 on a patient or performs a pre-scan procedure 208.

If an open of short circuit bias fault 210 occurs during either the pre-scan procedure or the scanning procedure, the CPU 28 logs and stores coil data which received via coil connector cable 46. A fault condition is detected by measuring the open current and the short current through the systems T/R bias circuitry 24. If the current falls outside a predetermined range, a fault condition is logged, however, data may be logged whether or not a fault condition occurs.

If a scanning procedure is taking place (e.g., during an active exam) and a coil is unplugged 214, a new or different coil is connected 212, or a change in the logical configuration occurs, an input event 202 is registered and the CPU 28 logs and stores coil data which is received through the coil connector cable 46.

Lastly, during a pre-scan or scanning operation, if a coil is disconnected, and then the same coil is reconnected using the same logical configuration, and the pre-scan or scan operation is successfully completed an input event 202 is registered and the CPU 28 logs and stores coil data which is received through the coil connector cable 46.

As data logs are constructed, the CPU 28 is further configured to algorithmically filter and analyzing the data logs, and more specifically, the input events 202, to create an output 216 which ultimately predicts a failure event of the at least one coil 22. In analyzing the data logs from input data, the CPU 28 is configured to elicit a quantified relationship between the input 202 and the data logs to categorically form an output 216, such that a failure of coil 22, whether it be a critical or non-critical failure, is predicted by making a future decision/assumption that may be then forwarded to an operator 48 who is capable of intervening before a critical failure occurs, which would lead to workflow disruption.

In this way, the CPU 28 is further configured to categorize the input events to provide the output 216, into which categories are implemented, e.g., category one 218 and category two, 220. In this exemplary embodiment, category one 218 are events that are grouped as operator induced faults 222, while category two are events grouped as hardware faults 224. In an exemplary embodiment of the present invention, the CPU 28 is configured to determining whether a fault is operator induced 222 or a hardware fault 224 in which the CPU 28 utilizes fault data signatures (e.g., recovery times), comparative historical data analysis, and parametric coil data, which are discussed in greater detail below.

If the CPU 28, via algorithmic analysis, categorizes an output result as a category one 218 operator induced fault 222, filter 226 filters out the operator induced fault 222, in part, based on fault recovery times. Category two faults 220, categorized as either hardware faults 224 or hardware failures 226, are thus analyzed independently of operator induced faults 222. For hardware faults 224, sub-categories 228 are derived based upon specific data signatures (e.g., data range values) that are identified by the CPU 28, each of which may indicate future issues with T/R bias operation.

Consequently, if a hardware fault 224 is detected, CPU 28 executes programmable instructions for a plurality of sub-categories 228, again, based on parametric data, historical analysis and specific fault data signatures. For each coil 22, the sub-categories are populated as "excluded (i.e. coil does not have enough data to analyze)" 230, "no reported faults" 232, "non-critical fault" 234, "critical fault" 236, and/or "last use critical open or short circuit fault" 238, each of which are explained in more detail below.

Sub-category populated as "excluded" 230 can represent at least two possibilities. A first possibility is that the operator chooses a coil configuration that has not been used for an extended period of time such that no data on the configuration exists and thus a statistically significant decision, and thus is subcategorized as "excluded". A second possibility is that he coil configuration has been used recently, but the logs lack sufficient data for analysis.

Sub-category populated as "no reported faults" 232 represents a multi-coil working to specification.

Sub-category populated as "non-critical fault" 234 can represent a number of possibilities. For example, it can represent a recoverable open circuit fault or a recoverable short circuit fault. As used herein, the term "recoverable fault" refers to a situation in which a coil, for at least a brief period of time, does not function to specification, but also does not critically fail. The term "recoverable fault" is also meant to include a coil that shows evidence of, for example, resistance that falls outside of coil specification, but only for a period of time, before it begins to work to specification again, without operator intervention or intervention from a technician. For example, "recoverable faults" are primarily ones that are operator induced where a poor physical connection between coil 18 and port 42 are made. These are made recoverable by the operator by re-connecting the coil 18 with port 42. Other "recoverable" faults may be due to slow degradations in components of the coil 18, or T/R bias circuitry that eventually may cause critical failures in the future. Other recoverable faults can be induced by timing errors from the T/R driver circuitry that can momentarily cause TR bias fault, but then quickly recovers.

Sub-category populated as "critical fault" 236 represents either a non-recoverable open circuit or short circuit failure 238, or a percent of coil failures above a predetermined threshold. Although as shown in FIG. 2 critical open or short circuit failure is shown as its own category, in an optional embodiment of the present invention, it may also be a sub-set of subcategory 236.

Once each sub-category has been populated based on the above-described guidelines, the CPU 28 is configured to filter the sub-categories 228 such that coils reported as not in use 230 and no reported faults 232 are filtered out, so that no further analysis is performed for that particular input event 202 cycle. The CPU 28 is programmed to conduct a predictive analysis by initiating a predetermined trigger event that corresponds to a particular data signature (e.g., as shown in FIGS. 5a-5c) for each of the sub-categories 228 of non-critical fault 234, critical fault 236, and critical open or short circuit fault 238.

As used herein, the term "trigger event" refers to the occurrence of a predetermined multi-coil or system coil parameter that prompts the CPU 28 to execute a plurality of predictive analysis functions to algorithmically predict future critical coil failures, and if necessary, contact a technician 48.

In an exemplary embodiment of the present invention, a first trigger event 240 is initiated for the open and short circuits faults 238 when predetermined amount of amperage varies by a predetermined amount, after either a critical or non-critical fault. For example, if the running mean per usage for open or short circuit currents vary by more than 30 mA, a trigger event 240 occurs. In another embodiment, a second trigger event 242 is initiated for critical open or short circuit faults 236. For example, in the event two or more critical faults occur within sliding six-usage window, that is, a predetermined percent of the critical failures occurs after six coil uses, a trigger event 242 occurs. In another embodiment, a third trigger event 244 is logged at the occurrence of a predetermined percent of non-critical failures. For example, if three or more recoverable faults occur within a sliding scale of six-usage window, a trigger event 244 occurs. It should be noted that triggers may vary based upon latency of data transfer, the rate of coil usage, and operator manipulation.

In the event of the occurrence of a trigger event 240-244, the CPU 28, which is connected to wireless router 36 having an antenna 38, and is configured to notify or alert a technician 48, via a wireless receiving device 46 such as personal digital assistants (PDA), cellular phone, smart phone, and the like. The CPU 28 is further configured to communicate to the technician 48 as to the type of fault that is occurring before a failure event occurs. In this way, the technician 48 can repair the MRI system 10, where needed, prior to system failure and workflow disruption. Furthermore, in an optional embodiment, the CPU 28 can also communicate to the technician if the system failure event occurs approximately concurrently with the hardware fault (e.g., in the event a system failure occurs within a relatively short time period after fault data is logged). In another optional embodiment, all logged data is sent to a remote location for storage and/or further analysis.

For purposes of data analysis, a display 34 is configured to provide graphical output to a user in the form of parametric data information, which includes alphanumeric (e.g., text, numbers, etc.) coil details, and graphical images (e.g., graphs and charts), etc. In one embodiment, display 34 is configured to also receive input from a user (e.g., touch screen, buttons located adjacent to the screen portion of display 34, etc.).

Figure 3:
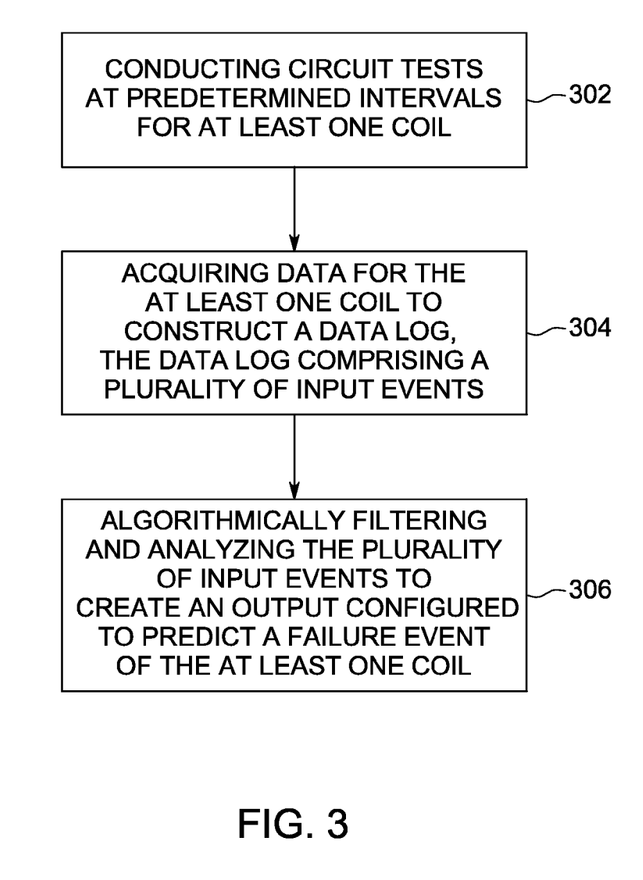
FIG. 3 is a flow-chart describing a step-wise method to analyze fault data for at least one coil on an MRI system in accordance with an embodiment of the present invention.

A method for acquiring and analyzing conditions for at least one coil of an MRI system is also provided herein. FIG. 3 is a flow chart of showing such a method 300. While the flowchart shows an exemplary step-by-step method, it is to be appreciated that a skilled artisan may rearrange or reorder the steps while maintaining like results.

Conducting circuit tests at predetermined intervals for the multi-coil array, block 302, includes, initially, determining which coils of the array are being used by an operator, and running circuit tests as described above with reference to FIG. 2.

Acquiring data for at least one coil to construct a data log populated by a plurality of input events, block 304, includes logging data at predetermined inputs events, again, such as those described in FIG. 2.

Algorithmically filtering and analyzing the plurality of input events to create an output configured to predict a failure event of the at least one coil, block 306 includes retrieving, by the CPU from the scanner, all of the data log files, storing the data log files, and analyzing the data logs files. By analyzing the data logs from input data, the CPU is configured to elicit a quantified relationship between the input and categorical output algorithmically, such that a failure of a coil, whether it be a critical or non-critical failure, is predicted by making a future decision/assumption that may be then forwarded to an operator who can intervene before a critical failure occurs that ultimately leads to workflow disruption.

In an exemplary embodiment of the present invention, determining whether a fault is operator induced or a hardware fault may comprise utilization of fault data signatures (e.g., recovery times), comparative historical data analysis, and parametric coil data, which are discussed in greater detail below.

The following examples serve to illustrate embodiments of the invention and are not intended to limit the same.

AN EXEMPLARY PROCESS FOR CONFIGURING TRIGGER EVENTS

Figure 4:
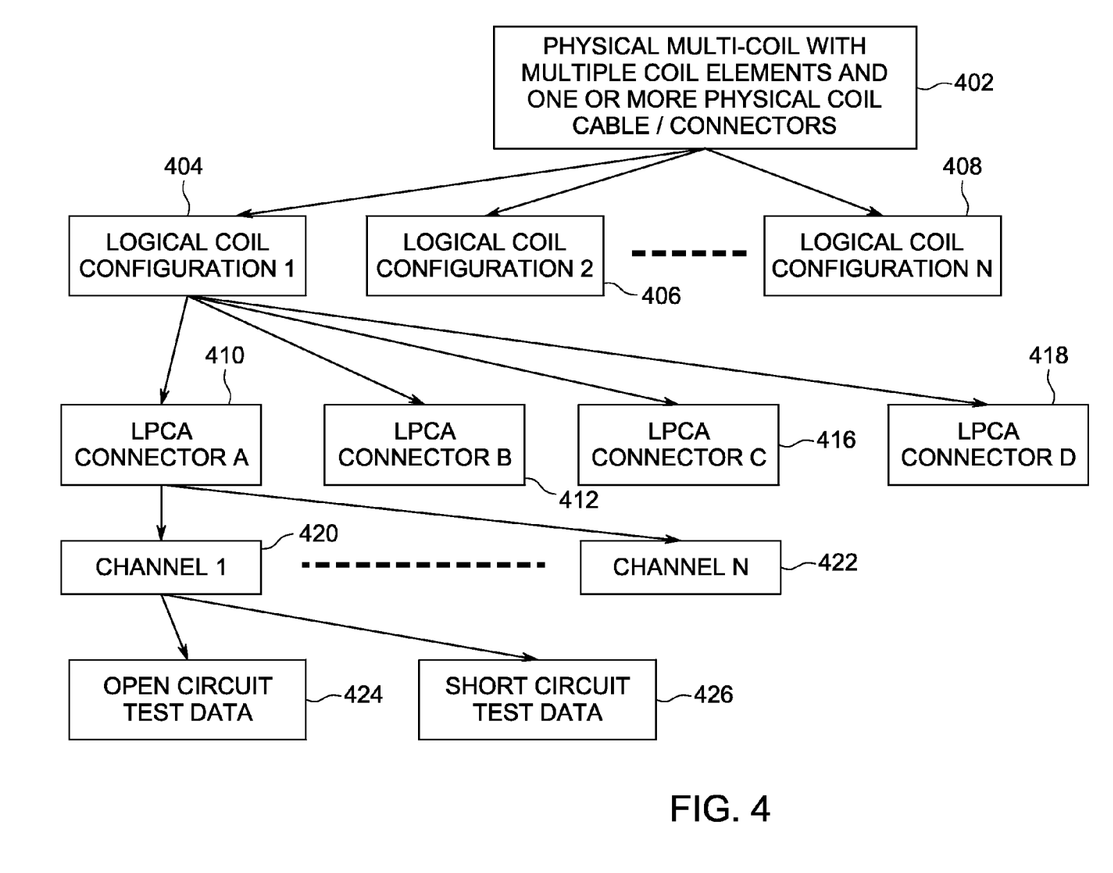
FIG. 4 is a block diagram of another exemplary MRI system in accordance with a further embodiment of the present invention.

FIG. 4 is a block diagram of exemplary coil configurations for use with the present invention, in which MR multi-coil T/R bias parametric data logs are log files resident on an MR system, for example, General Electric Signa® 1.5T/3.0T MR Systems, HDx/HDXt/MR750/MR450/MR450w, that record the open and short circuit bias currents for any multi-coil used on the scanner is represented at reference number 402. A multi-coil includes any transmit/receive, or receive only coil that is placed on the patient table or on the patient and physically plugged into one or more of the ports on the Low Profile Carriage Assembly (LPCA) or table Ports P3-P5. The LPCA can have up to 4 ports 410-418, labeled "A", "B", "C", "L" (for legacy), (or P1 and P2 for MR750/450/450w products). Each port can have anywhere from 8 to 32 receive channels, channel 1 referenced by 420 through channel N referenced by 422, based on different configurations, and for each channel open circuit test data 424 and short circuit test data 426. As shown in FIG. 4, it is helpful to logically view a multi-coil in a hierarchical format, but this is for illustration only, to show all possible combinations. In existing applications, multi-coils consist of a sub-set of these combinations.

Conducting circuit tests at predetermined intervals to construct a log file for each physical coil configuration uses a set of "rules" starting at the Logical Coil Configuration, through the individual open and short circuit current data for each valid LPCA "P" port, and each channel of each port.

Multi-Coil TR Bias Log File Descriptions

The multi-coil TR bias log files reside on the host computer, having one unique file for every physical coils logical configuration. Every physical coil connector has a unique "coil-ID" in the coils cable connector. Every coil-ID chip has a unique serial number, each with its own naming convention. Multi-coils that do not have coil ID chips (older coils) will produce log files with no unique serial number in the log file name.

In this exemplary embodiment, the data logging is event based driven and is logged to the file under these events conditions: Data is logged when (1) the multi-coil is first plugged in, (2) a new exam is done, (3) a pre-scan or scan operation is successfully completed, (4) upon the detection of any open or short circuit bias fault during pre-scan or scan, (5) if an exam is already active, and the multi-coil is unplugged, and a new different multi-coil is plugged in, (6) if the logical configuration is changed, (7) a pre-scan or scan task is successfully completed, (8) if an exam is already active, and the multi-coil is unplugged, and the same multi-coil is re-plugged in using the same logical configuration, and (9) a prescan or scan task is successfully completed:

Each "data sample" in the log files consists of these entries for each active LPCA port:

Channel N (Where N can be A, B, C, or L. This includes the active channels used for this LPCA port.)

Voltages N (Where N can be A, B, C, or L. This includes the voltages used on each channel during short and open circuit tests.

Open Circuit Currents N (Where N can be A, B, C, or L. This includes the measured current per channel for the open circuit forward bias test).

Short Circuit Currents N (Where N can be A, B, C, or L. This includes the measured current per channel for the short circuit reverse bias test).

Open Circuit Limit N (Where N can be A, B, C, or L. This includes the open circuit test limit per channel).

Short Circuit Limit N (Where N can be A, C, or L. This includes the short circuit test limit per channel).

The processor then, for each log file, analyzes all data to determine a fault or failure category for that file. The fault categories are as follows: excluded coil, no failures, non-critical failures, critical failures, and last use open or short, which is a subset of critical failure category. The processor performs an analysis routine for each log file, which are numbered 1-4, in which output categories include: 0—Not Applicable, 1—Excluded Log File, 2—No Failure Log File, 3—Non-Critical Failure Log File, 4—Critical Failure Log File. Other input parameters include multi-coil TR Bias log file name, number of days the coil is used (or not used), number of times the coil is used, number of minutes of open circuit error for critical error, the percent of failures based on times used, and which, if any, software updates or revisions took place.

Once the data logs are properly configured, algorithmic analysis, as described in the following steps may be executed. Initially, the processor determines the number of and unique names of LPCA ports used from data connectors, and for each LPCA port identified, keep a running count for each category and or sub-category 218-238. The CPU 28 then loops through each LPCA ports data with the following logic:

Sub-step A: Checks for imbalanced data matrices and exclude coil file if there is an imbalance;

Sub-step B: Checks change between first use and last use date and time. If it less than one day, increment an exclusion for that connector and skip to next connector;

Sub-step C: Checks all date and time stamps for each sample of LPCA connector grouping date and time stamps into "usage" bins by checking the change between the date and time stamps. If the change between corresponding date and time stamps exceeds 15 minutes, then a new usage count is logged;

Sub-step D: If usage count is less than two, increment an exclusion counter for that connector and skip to next connector;

Sub-step E: Checks for any short circuit failures;

Sub-step F: Checks the final data sample in the log for had any short circuit failures, and where detected, increments a last-use failure counter;

Sub-step G: For each coil usage group, checks for an open circuit failure. Open circuit failures are checked when the following usage group conditions are met: The group has only one sample long, the group is more than one sample long and the duration of the is group less than or equal to ten minutes, the group is more than one sample long and duration of group is greater than ten minutes, and if the open circuit failure lasts for more than ten minutes, the CPU increment a critical open circuit fail counter;

Sub-step H: Sets the return coil category based on predetermined values. For example, if a coil has been used less than or equal to one day or the number of coil uses is less than or equal to two uses, then the coil is in excluded category and is not analyzed. If coil has any occurrences of short circuit failures, then the coil is in the critical failure category. If the sum or individual counts of critical failures and non-critical failures are greater than or equal to ten percent of the coil uses, then coil is in the critical failure category. And lastly, if any coil/connector that has an open or short circuit fault as the last entry in the log file, then this coil is the last use failure category.

The CPU 28 is configured to run these predictive rules on log files that fall into the non-critical failures 234, critical failures 236 and last use open or short circuit failures 238. The CPU 28 further is configured to create a list of log files from the critical failure 234 and non-critical failure categories 236. The CPU 28 then runs each log file through the predictive function, defined as:

$$[\text{temp\_pred\_txt ec}] = \text{predict\_mc\_bias}(\text{pred\_log\_file\_list}(1,:), \text{usage\_minutes}, \text{mean\_current\_delta}, \text{usage\_window}, \text{code2\_count\_thresh}, \text{code1\_count\_thresh});$$

Where:
temp_pred_txt is the returned text for predictive triggers.
usage_minutes=15
mean_current_delta=30
usage_window=6
code2_count_thresh=2
code1_count_thresh=3

Based on the output of the predictive function, in the event of the occurrence of a trigger event 240-244, the CPU 28 notifies or alert a technician 48, via a wireless receiving device 46 as to the type of hardware fault before the failure event occurs. In this way, the technician 48 can repair the system, where needed, preferably prior to system failure and workflow disruption.

Specific configurations and arrangements of the claimed invention, discussed below with reference to the accompanying drawings, are for illustrative purposes only. Other configurations and arrangements that are within the purview of a skilled artisan can be made, used, or sold without departing from the spirit and scope of the appended claims. For example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise As used herein, an element or function recited in the singular and proceeded with the word "a" or "an" should be understood as not excluding plural said elements or functions, unless such exclusion is explicitly recited. Furthermore, references to "one embodiment" of the claimed invention should not be interpreted as excluding the existence of additional embodiments that also incorporate the recited features.

The construction and arrangement of the elements described herein are illustrative only. Although only a few embodiments have been described in detail in this disclosure, those of ordinary skill who review this disclosure will readily appreciate that many modifications are possible without materially departing from the novel teachings and advantages of the subject matter recited in the claims. Accordingly, all such modifications are intended to be included within the scope of the methods and systems described herein.

The order or sequence of any process or method steps may be varied or re-sequenced according to alternative embodiments. Other substitutions, modifications, changes and omissions may be made in the design, operating conditions and arrangement of the embodiments without departing from the spirit and scope of the methods and systems described herein.

What is claimed is:

1. A system for acquiring and analyzing fault conditions for at least one coil of an Magnetic Resonance Imaging (MRI) system, each of the at least one coils having a transmit/receive (T/R) bias circuit electrically connected to an interface, the system comprising:
   a central processing unit having a processor configured to execute programmable instructions, which when executed by the processor cause the processor to:
   conduct circuit tests at predetermined intervals for the at least one coil;
   acquire data for the at least one coil to construct a data log, the data log comprising a plurality of input events;

algorithmically filter and analyze the plurality of input events to create an output configured to predict a failure event of the at least one coil.

2. The system of claim 1, wherein the processor is further configured to:
categorize each of an operator induced fault or a hardware fault based on a fault recovery time, and if the fault recovery time is in a predetermined range of values, filter out the operator induced fault, where found.

3. The system of claim 1, wherein the processor is further configured to identify a type of hardware fault by comparing a present fault data signature with a plurality of predetermined data signatures and to categorize the types hardware fault.

4. The system of claim 1, wherein the processor is further configured to execute instructions to conduct a predictive analysis on the data logs, which when executed cause the processor to:
initiate a first trigger event for the open and short circuits that vary a predetermined amount of amperage after the fault;
initiate a second trigger event in an event of a predetermined percent of the critical failures; and
initiate a third trigger event in an event of a predetermined percent of the non-critical failures.

5. The system of claim 1, wherein the processor is further configured to:
communicate the output to a remote location and alert a technician as to the type of hardware fault before the failure events occurs.

6. The system of claim 1, wherein conducting circuit tests at predetermined intervals for the at least one coil comprises programming the processor to conduct multi-coil T/R bias open circuit tests and short circuit tests on the each of the coils.

7. The system of claim 1, wherein the MRI system comprises a low profile carriage assembly comprising a plurality of ports having a plurality of receive channels, the receive channels configured communicate data to form the data logs, wherein the data logs comprise a plurality of unique data logs that correspond to, respectively, each of the plurality of coils.

8. The system of claim 1, wherein the processor is further configured to log data at predetermined input event conditions comprising one or more of the following:
a plug-in;
a completed exam;
a pre-scan;
a detection of the open or short circuit bias fault;
a coil configuration change; and
an unplugging of one of the plurality of coils.

9. The system of claim 1, wherein the processor is further configured to monitor a usage rate and a relative usage rate of the at least one coils in the array of coils and prioritizing the coils such that the trigger events are automatically modified for the coils with usage rates above a predetermined rate.

10. A method for acquiring and analyzing conditions for at least one coil of Magnetic Resonance Imaging (MRI) system, each coil having a T/R bias circuit electrically connected to an interface; the method comprising:
conducting circuit tests at predetermined intervals for the at least one coil;
acquiring data for the at least one coil to construct a data log, the data log comprising a plurality of input events;
algorithmically filtering and analyzing the plurality of input events with a central processing unit to create an output configured to predict a failure event of the at least one coil.

11. The method of claim 10, wherein algorithmically filtering the plurality of input events further comprises:
categorizing each of an operator induced fault or a hardware fault based on fault recovery time, and filtering out the operator induced faults.

12. The method of claim 10, further comprising:
identifying a type of hardware fault by comparing a present fault data signature with a plurality of predetermined data signatures.

13. The method of claim 10, wherein algorithmically filtering the plurality of input events comprises conducting a predictive analysis on the data logs, the predictive analysis comprising:
initiating a first trigger event for the open and short circuits that vary a predetermined amount of amperage after the fault;
initiating a second trigger event in an event of a predetermined percent of the critical failures; and
initiating a third trigger event in an event of a predetermined percent of the non-critical failures.

14. The method of claim 10, further comprising:
communicating the output to a remote location and alerting a technician as to the type of hardware fault before the failure events occurs.

15. The method of claim 10, wherein conducting circuit tests further comprises:
automatically conducting multi-coil T/R bias open circuit tests and short circuit tests on the each of the coils at predetermined intervals.

16. The method of claim 10, wherein acquiring data logs comprises:
connecting the processor to a low profile carriage assembly comprising a plurality of ports having a plurality of receive channels, the receive channels configured communicate data to the processor.

17. The method of claim 10, wherein constructing a data log comprises logging data at predetermined input event conditions comprising one or more of the following:
a plug-in;
an completed exam;
a pre-scan;
a detection of the open or short circuit bias fault;
a coil configuration change; and
an unplugging of one of the plurality of coils.

18. The method of claim 10, further comprising:
monitoring a usage rate and a relative usage rate of the at least one coil in an array of coils and prioritizing the coils such that the trigger events are automatically modified trigger for the coils with usage rates above a predetermined rate.

19. The method of claim 10, wherein the at least one coil comprises a transmit/receive coil or a receive only coil.

20. The method of claim 10, wherein acquiring fault data comprises:
providing coil identification units for each of the at least one coils, the identification units being configured to communicate data to the processor.

* * * * *

UNITED STATES PATENT AND TRADEMARK OFFICE
CERTIFICATE OF CORRECTION

PATENT NO. : 8,515,696 B2
APPLICATION NO. : 13/009942
DATED : August 20, 2013
INVENTOR(S) : Huff et al.

Page 1 of 2

It is certified that error appears in the above-identified patent and that said Letters Patent is hereby corrected as shown below:

In the Specification

In Column 2, Line 64, delete "imaging" and insert -- Imaging --, therefor.

In Column 3, Line 50, delete "cod that" and insert -- coil that --, therefor.

In Column 3, Line 56, delete "RE Switch" and insert -- RF Switch --, therefor.

In Column 4, Line 25, delete "As such" and insert -- As such, --, therefor.

In Column 4, Line 30, delete "has it's" and insert -- has its --, therefor.

In Column 4, Line 31, delete "has it's" and insert -- has its --, therefor.

In Column 6, Line 1, delete "that he" and insert -- that the --, therefor.

In Column 8, Line 7, delete ""C", "L"" and insert -- "C", or "L" --, therefor.

In Column 8, Line 16, delete "consist" and insert -- will consist --, therefor.

In Column 8, Line 21, delete "LPCA "P"" and insert -- LPCA or "P" --, therefor.

In Column 8, Line 26, delete "file" and insert -- log file --, therefor.

In Column 8, Line 61, delete "A, C," and insert -- A, B, C, --, therefor.

In Column 9, Line 61, delete "critical failure 234 and non-critical failure categories 236." and insert -- critical failure 236 and non-critical failure categories 234. --, therefor.

Signed and Sealed this
Tenth Day of December, 2013

Margaret A. Focarino
*Commissioner for Patents of the United States Patent and Trademark Office*

CERTIFICATE OF CORRECTION (continued)
U.S. Pat. No. 8,515,696 B2

In Column 10, Line 31, delete "otherwise" and insert -- otherwise. --, therefor.

In the Claims

In Column 11, Line 13, in Claim 3, delete "types" and insert -- types of --, therefor.

In Column 11, Line 59, in Claim 10, delete "interface;" and insert -- interface, --, therefor.

In Column 12, Line 45, in Claim 17, delete "an completed" and insert -- a completed --, therefor.